(12) United States Patent
Boehm et al.

(10) Patent No.: US 7,686,014 B2
(45) Date of Patent: Mar. 30, 2010

(54) NEBULIZER-CONNECTING DEVICE FOR RESPIRATORS

(75) Inventors: Andreas Boehm, Reichling (DE); Frank Kummer, München (DE); Markus Mornhinweg, Diessen (DE)

(73) Assignee: Pari GmbH Spezialisten fur Effective Inhalation, Starnberg (DE)

( * ) Notice: Subject to any disclaimer, the term of this patent is extended or adjusted under 35 U.S.C. 154(b) by 859 days.

(21) Appl. No.: 10/554,884

(22) PCT Filed: May 6, 2004

(86) PCT No.: PCT/EP2004/004842

§ 371 (c)(1),
(2), (4) Date: Jul. 21, 2006

(87) PCT Pub. No.: WO2004/098689

PCT Pub. Date: Nov. 18, 2004

(65) Prior Publication Data

US 2007/0119449 A1 May 31, 2007

(30) Foreign Application Priority Data

May 6, 2003 (DE) ................................ 103 20 143

(51) Int. Cl.
*A62B 9/04* (2006.01)
(52) U.S. Cl. .............................. 128/200.27; 128/205.24
(58) Field of Classification Search ............ 128/200.11, 128/200.14, 200.18, 200.21–200.24, 201.28, 128/202.28, 203.11, 203.12, 203.15, 203.16, 128/203.29, 204.18, 204.25, 205.24, 206.15, 128/207.12, 207.16; 137/843–850
See application file for complete search history.

(56) References Cited

U.S. PATENT DOCUMENTS

| | | | | |
|---|---|---|---|---|
| 584,091 | A | * | 6/1897 | Leidich ........................ 137/849 |
| 2,688,979 | A | * | 9/1954 | Kendrick ................ 137/512.15 |
| 2,710,623 | A | * | 6/1955 | Kolos ........................... 137/223 |
| 2,822,819 | A | * | 2/1958 | Geeraert ....................... 137/844 |
| 3,174,434 | A | * | 3/1965 | Schieve ........................ 415/146 |
| 3,279,487 | A | | 10/1966 | Elam |
| 4,077,404 | A | | 3/1978 | Elam |
| 4,314,586 | A | | 2/1982 | Folkman |
| 4,510,933 | A | | 4/1985 | Wendt et al. |

(Continued)

FOREIGN PATENT DOCUMENTS

DE 42 32 082 A1 3/1994

(Continued)

*Primary Examiner*—Steven O Douglas
(74) *Attorney, Agent, or Firm*—Merchant & Gould P.C.

(57) ABSTRACT

The aim of the invention is to connect a nebulizer to a breathing air tube of a respirator. This aim is achieved by a nebulizer-connecting device that has a breathing air-directing unit that is provided with a first mechanism for connecting a duct supplying breathing air, a second mechanism for connecting a duct evacuating breathing air, and a third mechanism for connecting the nebulizer, and a sealing unit which is arranged on the third connecting mechanism and by which a flow path for an aerosol generated by the nebulizer can be unblocked when the nebulizer is connected while the flow path for an aerosol generated by the nebulizer can be sealed therewith when the nebulizer is removed. A sealing member is opened when the nebulizer is connected while being closed when the nebulizer is removed.

6 Claims, 15 Drawing Sheets

U.S. PATENT DOCUMENTS

| | | | |
|---|---|---|---|
| 4,951,661 A | | 8/1990 | Sladek |
| 5,443,452 A | * | 8/1995 | Hart et al. ............... 604/167.03 |
| 6,135,108 A | | 10/2000 | Hoenig |
| 6,382,255 B2 | * | 5/2002 | McFarland .................. 137/849 |
| 6,725,858 B2 | * | 4/2004 | Loescher ............... 128/200.14 |
| 2002/0020409 A1 | | 2/2002 | Kidwell et al. |
| 2003/0222238 A1 | * | 12/2003 | Getzewich et al. .......... 251/342 |

FOREIGN PATENT DOCUMENTS

| | | |
|---|---|---|
| DE | 93 20 493.0 | 10/1994 |
| DE | 196 39 870 | 12/1997 |
| DE | 103 20 143 A1 | 12/2004 |
| EP | 0 576 380 A1 | 12/1993 |
| EP | 0 579 380 A1 | 12/1993 |
| FR | 1 449 918 | 7/1965 |
| FR | 1 552 128 | 11/1967 |
| FR | 2 267 801 | 11/1975 |
| FR | 2 804 609 | 8/2001 |
| WO | WO 01/41853 A1 | 6/2001 |
| WO | WO 02/089887 A1 | 11/2002 |
| WO | WO 2004/098689 A1 | 11/2004 |

* cited by examiner

NEBULIZER-CONNECTING DEVICE FOR RESPIRATORS

BACKGROUND

The present invention relates to a nebulizer-connecting device for respirators and generally for devices in which a user is supplied with breathing air via a delivery duct, for example a hose line.

In respirators, a patient who is to be respirated is supplied with breathing air via a hose line. In order to be able to add an aerosol to the breathing air, a nebulizer must be connected to the hose line in such a way that the aerosol generated by the nebulizer enters the breathing air delivered to the patient. As known from U.S. Pat. No. 4,951,661 or WO 02/089887, a nebulizer may be connected to the breathing-air duct by means of a T-fitting inserted in the hose line so that the aerosol flows through the tube section which discharges vertically into the tube section carrying the breathing air. In this way, the aerosol generated enters the breathing-air flow and is supplied via the delivery hose line together with the respiration air to the patient.

However, in clinical practice, for reasons of cost alone, nebulizers cannot be permanently connected, but have to be removed from the respiration air duct again when the aerosol therapy has been completed. The insertion and removal of the T-fitting with the nebulizer connected thereto is problematical since to do this it is necessary to interrupt the breathing air supply through the delivery duct from the respirator to the patient. Even if it is attempted to keep the interruption very brief, insertion and removal in this manner is not acceptable. Even without the separation of the respirator hose line, however, the attachment and removal of the nebulizer from the connecting fitting causes problems, since for a short time the T-fitting on the vertically extending connecting fitting is open, which impairs the patient's respiration. In addition, this method does not ensure that the connecting fitting is sealed again after the removal of the nebulizer, for example with a stopper. Some of these problems are also addressed in U.S. Pat. No. 4,951,661 or WO 02/089887.

Known from U.S. Pat. No. 4,951,661 is a T-fitting with a valve which seals the T-connector when no nebulizer is connected; in the sealed position, the valve element is secured by the action of a spring. Connecting a nebulizer to the T-connector causes the valve element to be lifted against the action of the spring. The T-fitting design known from U.S. Pat. No. 4,951,661 is unfavourable for several reasons. The valve element's spring is arranged in the aerosol's flow path and thus impedes the supply of the aerosol. In addition, the spring becomes contaminated and is difficult to clean. The lifting of the valve element is performed by means of a punch which is also located in the flow path of the aerosol and disrupts the flow. In addition, the lifted valve element is arranged in the breathing-air flow and hence also impedes the flow here as well.

In order to rectify some of the errors in the design known from U.S. Pat. No. 4,951,661, WO 02/089887 proposes that the spring for the valve element is not arranged centrally in the T-connector around the punch shaft but in a housing arranged around the wall of the T-connector. This ensures that the spring is arranged in an enclosed space and hence cannot become contaminated. However, the design known from WO 02/089887 is still unfavourable since once again the punch, the punch shaft and the valve element are arranged so that they impede the flow thus causing aerosol losses since the aerosol is readily precipitated on the numerous surfaces arranged in the flow path. The spring housing causes the T-connector to be narrowed. In addition, in lifted condition, the valve element is in the flow path of the breathing air.

It should be noted with regard to both constructions that due to the spring, which has an indispensable restoring force in order to prevent the T-fitting remaining open after the removal of the nebulizer, both designs are very complicated and present problems with regard to cleaning and sterilisation.

SUMMARY

Against this background, the technical problem to be solved by the invention is to provide a nebulizer connecting device for respirators or similar that facilitates the simple connection and removal of a nebulizer so that an aerosol can be supplied to the breathing air, but in which it is ensured that, during the connection and removal of the nebulizer, there is no interruption to and no impairment of the breathing air supply, which has a simple design and in which there are no flow-impeding influences.

This problem is solved by a nebulizer-connecting device for respirators or similar with a breathing air-directing unit with a first connecting mechanism for connecting a duct supplying breathing air, a second connecting mechanism for connecting a duct evacuating breathing air and a third connecting mechanism for connecting a nebulizer and a sealing unit which is arranged on the third connecting mechanism and by means of which a flow path for an aerosol generated by the nebulizer can be unblocked when the nebulizer is connected and by means of which the flow path for an aerosol generated by the nebulizer can be sealed when the nebulizer is removed.

According to the invention, the sealing unit, which is arranged on the connecting mechanism for the nebulizer on the breathing air-directing unit, is opened or closed on the connection and removal respectively of the nebulizer so that the processes are closely linked with each other. This will ensure that the arrangement according to the invention guarantees that the possibility of connection without opening and removal without sealing is virtually excluded.

Advantageously, the nebulizer, or a part thereof, for example an aerosol delivery fitting, acts on the sealing unit in such a way that the flow path for the aerosol is opened or closed. This ensures that the sealing unit can be actuated without any further aids when the nebulizer is connected.

In an advantageous embodiment, the sealing unit comprises a sealing member in a sealing member housing, in which the sealing member may be moved by means of the nebulizer, or a part thereof, out of a position in which the sealing member seals the flow path of an aerosol generated by the nebulizer into the breathing air-directing unit, into a position in which the sealing member unblocks the flow path of an aerosol generated by the nebulizer into the breathing air-directing unit and back.

The design of the dimensions of an opening in the sealing member housing, into which the aerosol delivery fitting of a nebulizer is inserted and a notch on the aerosol delivery fitting enables it to be guaranteed in an advantageous embodiment that the nebulizer can only be removed if the sealing member is in the sealing position.

Further advantageous embodiments may be found in the subclaims and the description of the diagrams.

The invention may be used not only with respirators in which an interruption of or impairment to respiration can result in life-threatening situations. The connection device according to the invention can also be used with other types of medical technology, for example devices for breathing therapy or devices for pulmonary function measurements if an aerosol is added to the breathing air during a therapeutic or measuring process and for this a nebulizer is to be connected to a delivery duct for the breathing air.

BRIEF DESCRIPTION OF THE DRAWINGS

The invention will further be described with reference to examples of embodiments shown in the drawings. Here.

DETAILED DESCRIPTION

The following description of the examples of embodiments explains the use of the nebulizer-connecting device on a respirator according to the invention. However, this does not entail or intend any restriction to this application, even if the application of the nebulizer-connecting device according to the invention in a respirator respiration situation achieves particular advantages as will be evident from the explanation of the examples of embodiments.

First Example of an Embodiment

Figure 1:
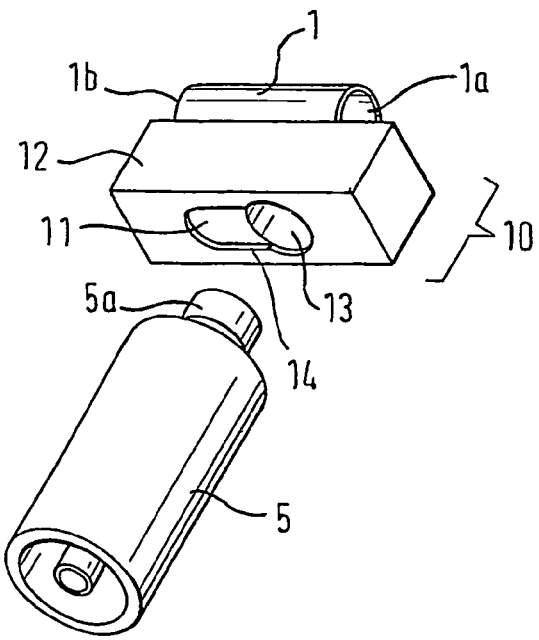
FIGS. 1 to 3 show a first example of an embodiment of the invention.
Figure 2:
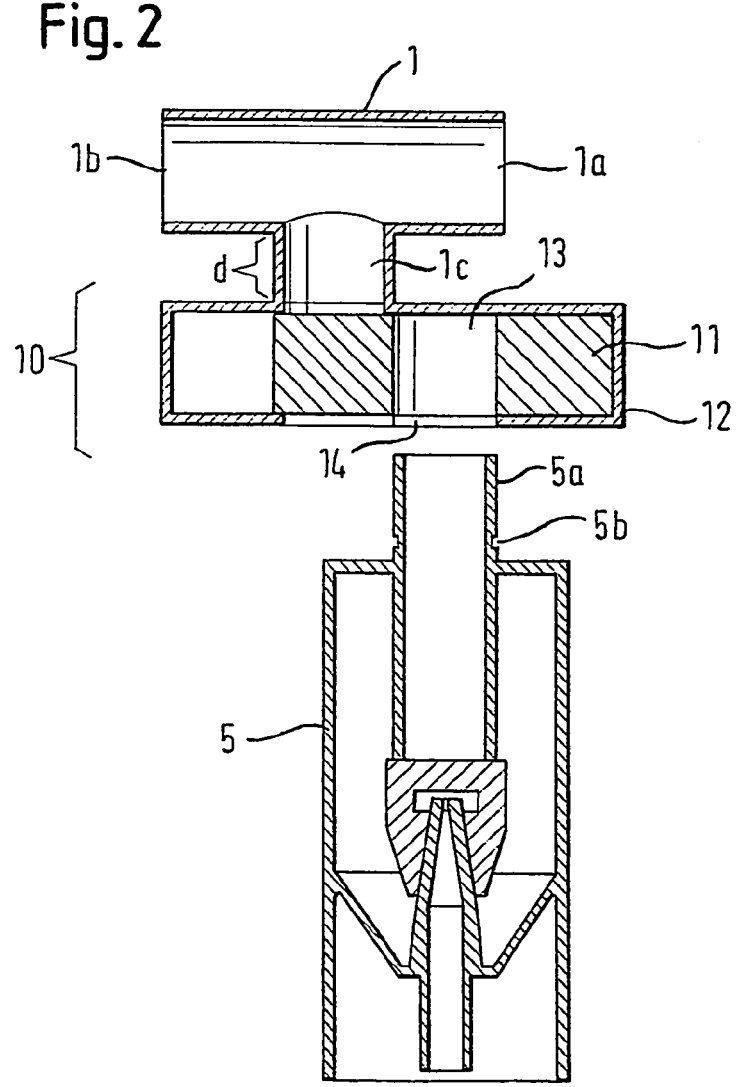
Figure 3:
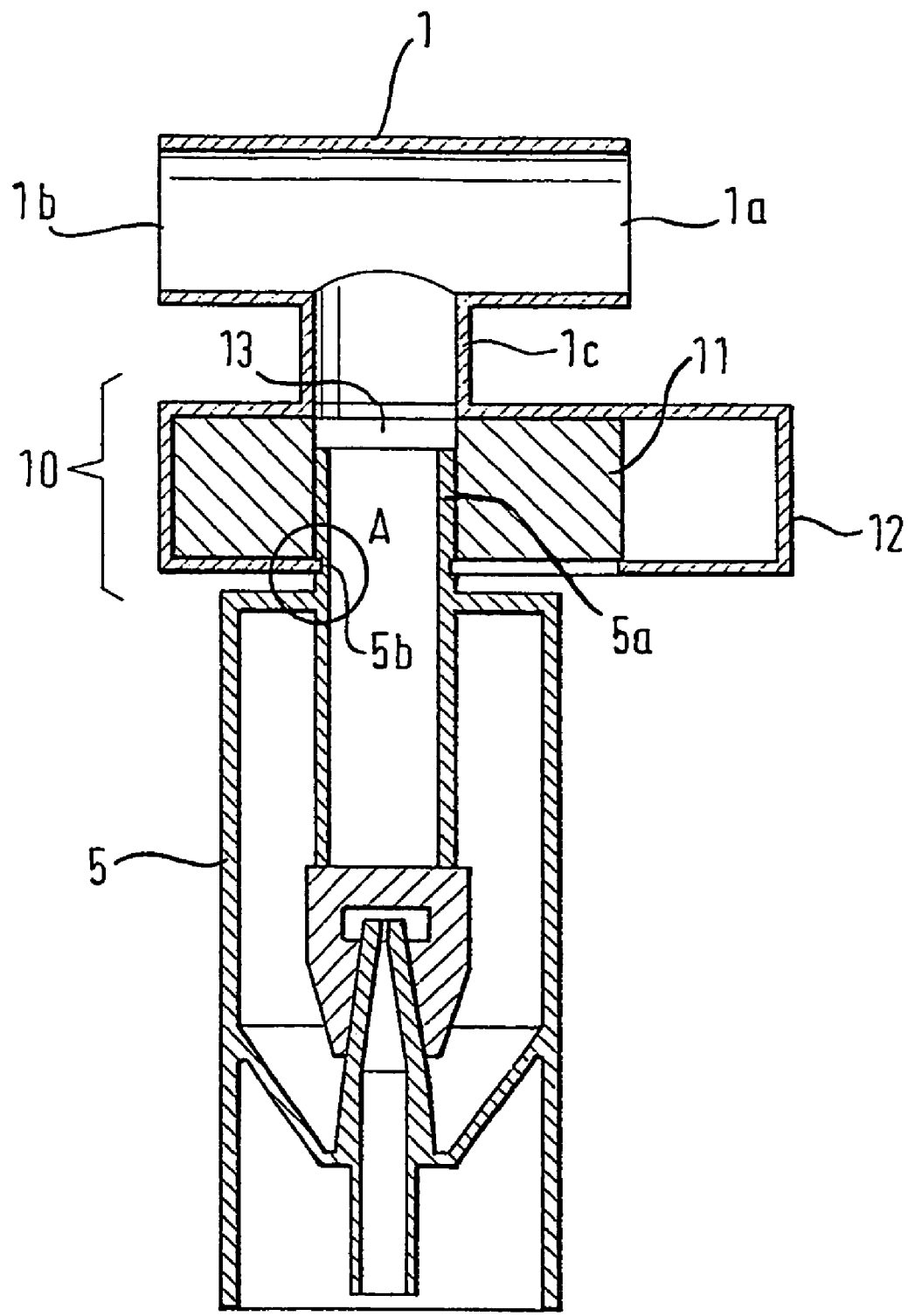

FIGS. 1 to 3 show a first example of an embodiment of a nebulizer-connecting device according to the invention for respirators or similar.

FIG. 1 shows a perspective view of the first example of an embodiment providing an aspect common to all examples of embodiments. This is because all examples of embodiments of the nebulizer-connecting device according to the invention have a breathing air-directing unit 1, for example the tube section 1 shown in FIG. 1, which is inserted in a breathing-air duct for the respiration air supplied by a respirator and delivered to a patient. A first connecting mechanism 1a, in the simplest case one of the two tube ends, is used to connect a breathing-air duct supplying respiration air, as a rule a hose, which is connected to a respirator. A second connecting mechanism 1b is used to connect a breathing-air duct evacuating respiration air, as a rule a hose, which delivers the respiration air to the patient.

As shown in FIGS. 2 and 3, according to the invention, a sealing unit 10 is arranged on a third connecting mechanism 1c, for example the tube section 1c shown in FIGS. 2 and 3, which discharges into the breathing air-directing unit 1. The sealing unit 10 in the first example of an embodiment according to the invention comprises a sealing member 11, which is arranged in a sealing member housing 12. FIG. 2 shows the sealing member 11 in the position which seals the flow path of the third connecting mechanism 1c. As FIG. 2 shows, a part of the sealing member 11 is arranged in front of the connector 1c so that through the connector 1c it is impossible for respiration air to enter the surroundings or surrounding air to enter the respiration air. The sealing member 11 comprises a sealing member opening 13 into which a delivery fitting 5a of a nebulizer 5 can be introduced. For this, the sealing member housing 12 has a sealing member housing opening 14, which is shaped so that a delivery fitting 5a of a nebulizer 5 can be introduced through the sealing member housing opening 14 into the sealing member opening 13 and the delivery fitting 5a can be displaced in such a way that the sealing member 11 is displaced in the sealing member housing 12. The rectilinear movement is defined by the rectangular design of both the sealing member 11 and the sealing member housing 12 shown in FIG. 1. As FIG. 1 also shows, the sealing member housing opening 14 is an elongated hole so that a cylindrical delivery fitting 5a of a nebulizer 5 can be introduced and displaced in a rectilinear way in the sealing member housing opening 14. As FIG. 3 shows, in the displaced position, the sealing member opening 13 is arranged opposite to the connector 1c so that the delivery fitting 5a of the nebulizer 5 is aligned with the connector 1c. In this way, an aerosol generated by the nebulizer travels in an undisrupted route from the nebulizer 5 through the delivery fitting 5a and the connector 1c into the breathing air-directing unit 1 of the nebulizer-connecting device according to the invention.

When the nebulizer 5 is removed, firstly the nebulizer 5 with the delivery fitting 5a is displaced into the position shown in FIG. 2, which causes the sealing member 11 to seal the third connecting mechanism 1c, as shown in FIG. 2. Then, the delivery fitting 5a of the nebulizer 5 is pulled out of the sealing member opening 13.

According to the invention, the third connecting mechanism 1c is sealed so that respiration air cannot enter the surroundings and surrounding air cannot enter the respiration air.

In order to avoid, in the position shown in FIG. 3, the delivery fitting 5a of the nebulizer 5 being unintentionally pulled out of the sealing member opening 13, the sealing member housing opening 14 is preferably narrower in an area facing the connector 1c than it is in an area which is aligned with the position of the sealing member opening 13 in the position shown in FIG. 2. The external diameter of the delivery fitting 5a is larger than the width of the sealing member housing opening 14 in the narrowed area. To enable the delivery fitting 5a of the nebulizer 5 to be displaced into the narrower area of the sealing member housing opening 14, the delivery fitting 5a has a notch 5b that reduces the outside dimension of the delivery fitting 5a sufficiently to enable it to be pushed into the narrower area of the sealing member housing opening 14. FIG. 3 shows at point A how the sealing member housing 12 engages in the notch 5b of the delivery fitting 5a, which prevents the delivery fitting 5a of the nebulizer 5 being pulled out of the sealing member opening 13 in the position shown in FIG. 3. Since the narrow area of the sealing member housing opening 14 extends far enough to ensure that the engagement of the sealing member housing 12 in the notch 5b of the delivery fitting 5a is only cancelled when the sealing member 11 has reached the position shown in FIG. 2, it is also ensured that in an intermediate position between the nebulizing position of the sealing member 11 according to FIG. 3 and the sealing position of the sealing member 11 according to FIG. 2, the delivery fitting 5a of the nebulizer cannot be pulled out of the sealing member opening 13.

As FIG. 2 shows, the distance d between the sealing unit 10 and the breathing air-directing unit 1 of the nebulizer-connecting device according to the invention may be shortened by virtually any amount. If the distance d is minimized, i.e. if the sealing unit 10 is arranged directly next to the breathing air-directing unit 1, virtually no dead volume forms in the closed condition and the respiration air flowing through the breathing air-directing unit 1 is not impaired. In addition, the flow path for the aerosol flowing through the delivery fitting 5a from the nebulizer into the respiration air is minimized when the distance d is shortened as much as possible.

Second Example of an Embodiment

Figure 4:
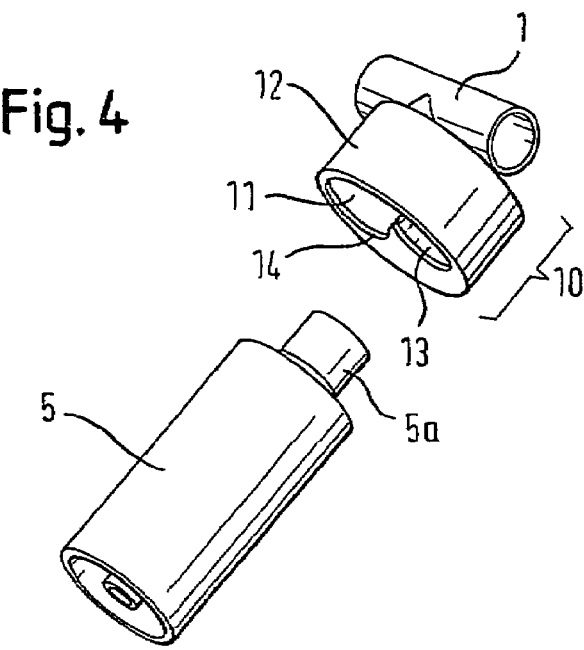
FIGS. 4 to 6 show a second example of an embodiment of the invention.
Figure 5:
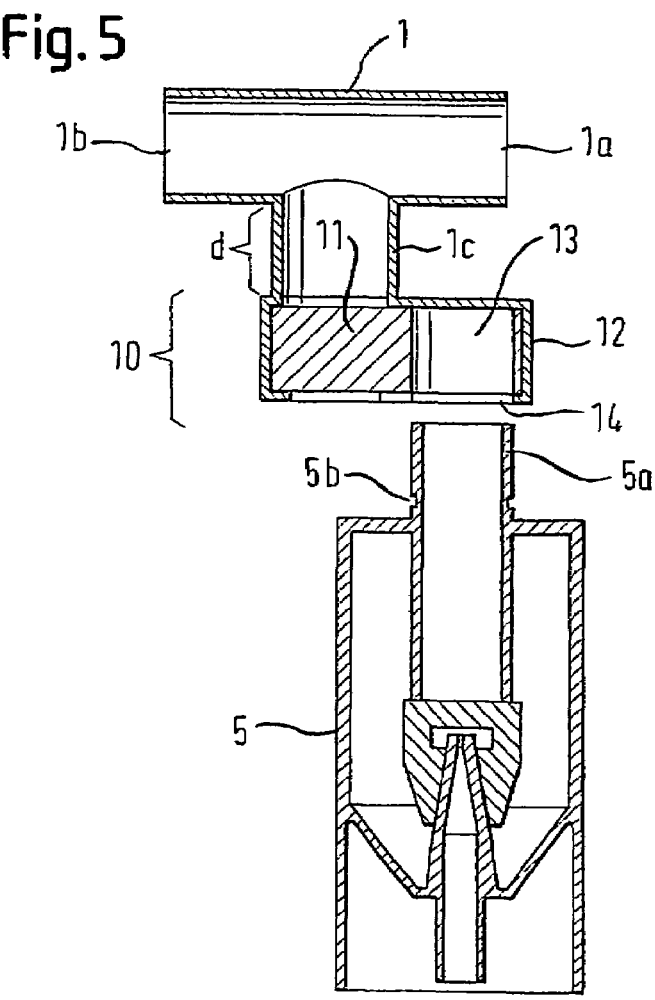
Figure 6:
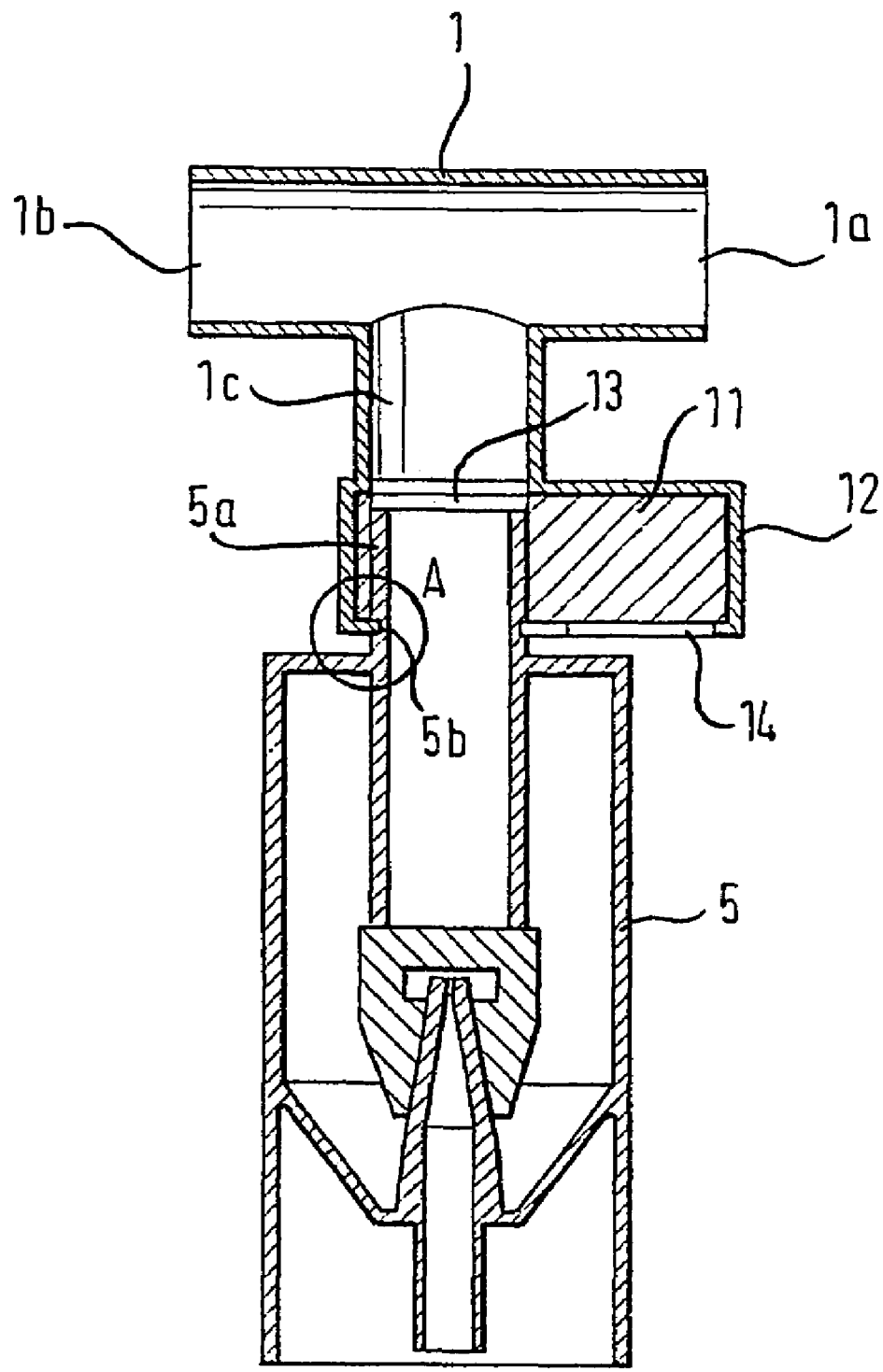

FIGS. 4 to 6 show a second example of an embodiment of a nebulizer-connecting device according to the invention for respirators or similar.

FIGS. 4 to 6 firstly show that, like the other examples of embodiments, the second example of an embodiment comprises a breathing air-directing unit 1, for example the tube section 1 shown in FIG. 4, which is inserted into a duct for the respiration air supplied by a respirator and delivered to a patient. A first connecting mechanism 1a, in the simplest case one of the two tube ends, is used to connect a breathing-air duct supplying respiration air, as a rule a hose, which is connected to a respirator. A second connecting mechanism 1b is used to connect a breathing-air duct evacuating respiration air, as a rule a hose, which delivers the respiration air to the patient.

As shown in FIGS. 5 and 6, according to the invention, a sealing unit 10 is arranged on a third connecting mechanism 1c, for example the tube section shown in FIGS. 5 and 6 which discharges into the breathing air-directing unit 1. The sealing unit 10 in the second example of an embodiment according to the invention comprises a sealing member 11, which is arranged in a sealing member housing 12. FIG. 5 shows the sealing member 11 in the position which seals the flow path of the third connecting mechanism 1c. As FIG. 5 shows, part of the sealing member 11 is arranged before the connector 1c so that through the connector 1c it is impossible for respiration air to enter the surroundings or surrounding air to enter the respiration air. The sealing member 11 comprises a sealing member opening 13 into which a delivery fitting 5a of a nebulizer 5 may be introduced. For this, the sealing member housing 12 has a sealing member housing opening 14 which is shaped so that the delivery fitting 5a of the nebulizer 5 can be introduced through the sealing member housing opening 14 into the sealing member opening 13 and the delivery fitting 5a may be moved along a circular segment in such a way that the sealing member 11 is rotated in the sealing member housing 12. The movement along a circular path is defined by the cylindrical design of both the sealing member 11 and the sealing member housing 12 which is shown in FIG. 4. As is also shown in FIG. 4, the sealing member housing opening 14 is an elongated hole extending along a circular segment so that a cylindrical delivery fitting 5a of a nebulizer 5 can be introduced and moved in the sealing member housing opening 14 along a circular path. As FIG. 6 shows, in rotated position, the sealing member opening 13 is arranged opposite the connector 1c so that the delivery fitting 5a of the nebulizer 5 is aligned with the connector 1c. In this way, an aerosol generated by the nebulizer travels in an undisrupted route from the nebulizer 5 through the delivery fitting 5a and the connector 1c into the breathing air-directing unit 1 of the nebulizer-connecting device according to the invention.

When the nebulizer 5 is removed, firstly the nebulizer 5 with the delivery fitting 5a is moved into the position shown in FIG. 5, which causes the sealing member 11 to seal the third connecting mechanism 1c, as shown in FIG. 5. Then, the delivery fitting 5a of the nebulizer 5 is pulled out of the sealing member opening 13. According to the invention, the third connecting mechanism 1c is now sealed so that respiration air cannot enter the surroundings and surrounding air cannot enter the respiration air.

In order to avoid, in the position shown in FIG. 6, the delivery fitting 5a of the nebulizer 5 being unintentionally pulled out of the sealing member opening 13, the sealing member housing opening 14 is narrower in an area facing the connector 1c than it is in an area which is aligned with the position of the sealing member opening 13 in the position shown in FIG. 5. The external diameter of the delivery fitting 5a is larger than the width of the sealing member housing opening 14 in the narrowed area. To enable the delivery fitting 5a of the nebulizer 5 to be moved into the narrower area of the sealing member housing opening 14, the delivery fitting 5a has a notch 5b that reduces the outside dimension of the delivery fitting 5a sufficiently to enable it to be pushed into in the narrower area of the sealing member housing opening 14. FIG. 6 shows at point A how the sealing member housing 12 engages in the notch 5b of the delivery fitting 5a which prevents the delivery fitting 5a of the nebulizer 5 being pulled out the sealing member opening 13 in the position shown in FIG. 6. Since the narrow area of the sealing member housing opening 14 extends far enough to ensure that the engagement of the sealing member housing 12 in the notch 5b of the delivery fitting 5a is only cancelled when the sealing member 11 has reached the position shown in FIG. 5, it is also ensured that in an intermediate position between the nebulizing position of the sealing member 11 according to FIG. 6 and the sealing position of the sealing member 11 according to FIG. 5, the delivery fitting 5a of the nebulizer 5 cannot be pulled out of the sealing member opening 13.

As FIG. 5 shows, the distance d between the sealing unit 10 and the breathing air-directing unit 1 of the nebulizer-connecting device according to the invention may be shortened by virtually any amount. If the distance d is minimized, i.e. if the sealing unit 10 is arranged directly next to the breathing air-directing unit 1, virtually no dead volume forms in the closed condition and the respiration air flowing through breathing air-directing unit 1 is not impaired. In addition, the flow path for the aerosol flowing through the delivery fitting 5a from the nebulizer into the respiration air is minimized when the distance d is shortened as much as possible.

Third Example of an Embodiment

Figure 7:
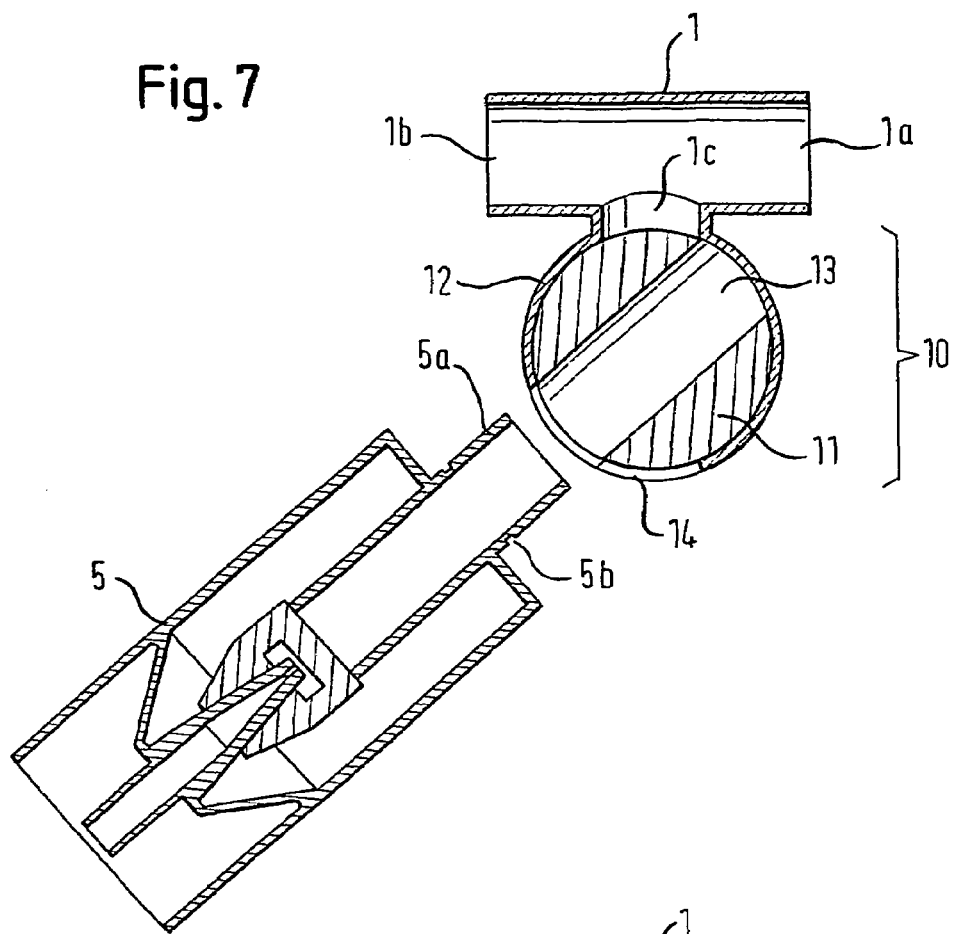
FIGS. 7 to 9 show a third example of an embodiment of the invention.
Figure 8:
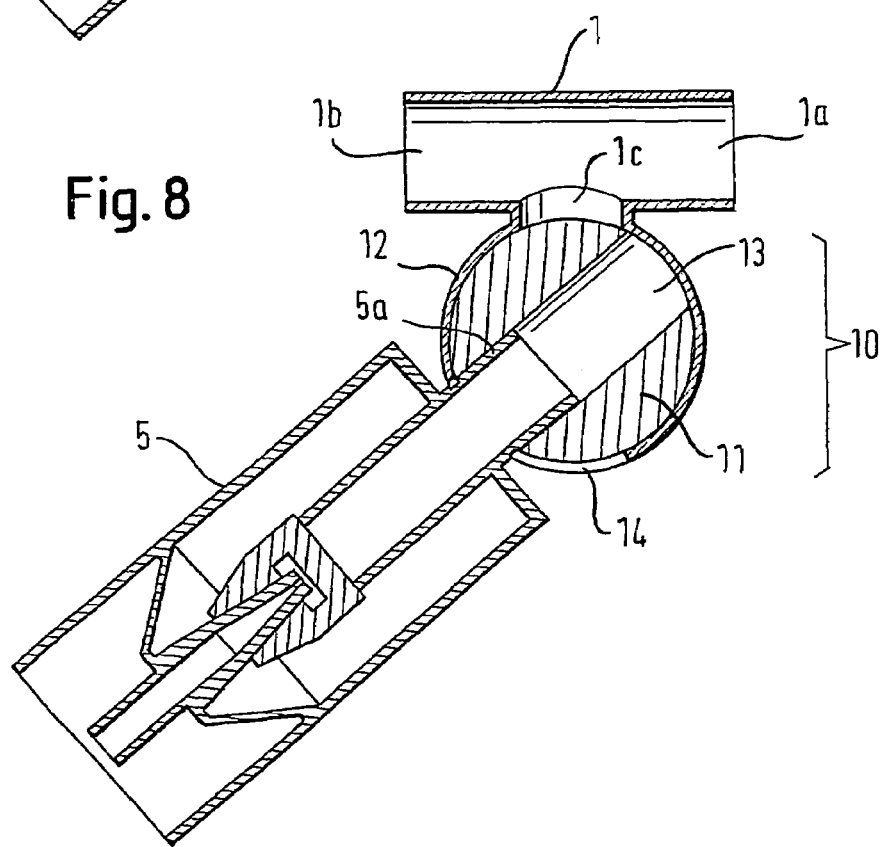
Figure 9:
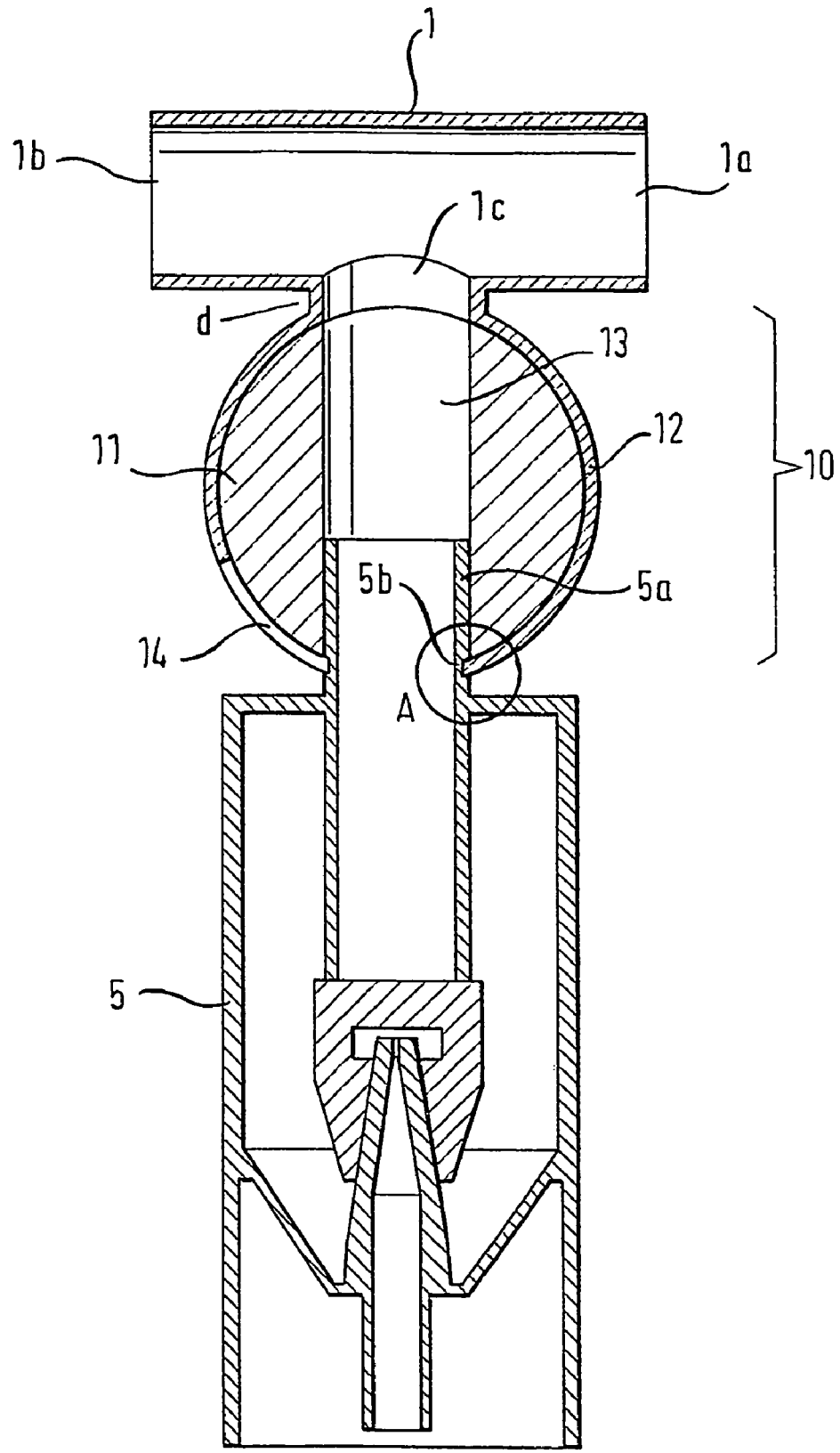

FIGS. 7 to 9 show a third example of an embodiment of a nebulizer-connecting device according to the invention for respirators or similar.

FIGS. 7 to 9 firstly show that, like the other examples of embodiments, the third example of an embodiment comprises a breathing air-directing unit 1, for example the tube section 1 shown in FIG. 7, which is inserted in a duct for the respiration air supplied by a respirator and delivered to a patient. A first connecting mechanism 1a, in the simplest case one of the two tube ends, is used to connect a breathing-air duct supplying respiration air, as a rule a hose, which is connected to a respirator. A second connecting mechanism 1b is used to connect a breathing-air duct evacuating respiration air, as a rule a hose, which delivers the respiration air to the patient.

As shown in FIGS. 7 to 9, a sealing unit 10 is arranged on a third connecting mechanism 1c, for example the tube section shown in FIGS. 7 to 9, which discharges into the breathing air-directing unit 1, according to the invention. The sealing unit 10 in the third example of an embodiment according to the invention comprises a sealing member 11, which is arranged in a sealing member housing 12. FIGS. 7 and 8 show the sealing member 11 in the position which seals the flow path of the third connecting mechanism 1c. As FIGS. 7 and 8 show, a part of the sealing member 11 is arranged before the connector 1c so that through the connector 1c it is impossible for respiration air to enter the surroundings or surrounding air to enter the respiration air.

The sealing member 11 comprises a sealing member opening 13, into which a delivery fitting 5a of a nebulizer 5 may be introduced. FIG. 7 shows the nebulizer 5 before the delivery fitting 5a was inserted in the sealing member opening 13; FIG. 8 shows the nebulizer 5 after the delivery fitting 5a was inserted in the sealing member opening 13. In order to facilitate the insertion, the sealing member housing 12 has a sealing member housing opening 14 which is shaped so that the delivery fitting 5a of the nebulizer 5 can be introduced through the sealing member housing opening 14 into the sealing member opening 13 and the delivery fitting 5a moved along a circular segment in such a way that the sealing member 11 is turned in the sealing member housing 12. The turning motion is defined by a cylindrical or spherical shape of both the sealing member 11 and the sealing member housing 12. FIGS. 7 to 9 show cross sections corresponding to both a flat cylindrical shape and a spherical shape of sealing member 11 and sealing member housing 12. As shown in FIGS. 7 to 9, the sealing member housing opening 14 is an elongated hole extending in the jacket or ball surface so that a cylindrical delivery fitting 5a of a nebulizer 5 may be introduced and swivelled in the sealing member housing opening 14. As shown in FIG. 9, in the swivelled position, the sealing member opening 13 is arranged opposite to the connector 1c so that the delivery fitting 5a of the nebulizer 5 is aligned with the connector 1c. In this way, the aerosol generated by the nebulizer travels in an undisrupted route from the nebulizer 5 through the delivery fitting 5a and the connector 1c into the breathing air-directing unit 1 of the nebulizer-connecting device according to the invention.

When the nebulizer 5 is removed, firstly, the nebulizer 5 with the delivery fitting 5a is moved into the position shown in FIG. 8, which causes the sealing member 11 to seal the third connecting mechanism 1c as shown in FIG. 8. Then, the delivery fitting 5a of the nebulizer 5 is pulled out of the sealing member opening 13 as shown in FIG. 7. According to the invention, the third connecting mechanism 1c is then sealed so that respiration air cannot enter the surroundings and surrounding air cannot enter the respiration air.

In order to avoid, in the position shown in FIG. 9, the delivery fitting 5a of the nebulizer 5 being unintentionally pulled out of the sealing member opening 13, the sealing member housing opening 14 is narrower in an area facing the connector 1c than it is in an area which is aligned with the position of the sealing member opening 13 in the position shown in FIG. 7 or 8. The external diameter of the delivery fitting 5a is larger than the width of the sealing member housing opening 14 in the narrowed area. To enable the delivery fitting 5a of the nebulizer 5 to be swivelled into the narrower area of the sealing member housing opening 14, the delivery fitting 5a has a notch 5b that reduces the outside dimension of the delivery fitting 5a sufficiently, to enable it to be pushed into the narrower area of the sealing member housing opening 14. FIG. 9 shows at point A how the sealing member housing 12 engages in the notch 5b of the delivery fitting 5a which prevents the delivery fitting 5a of the nebulizer 5 being pulled out of the sealing member opening 13 in the position shown in FIG. 9. Since the narrow area of the sealing member housing opening 14 extends far enough to ensure that the engagement of the sealing member housing 12 in the notch 5b of the delivery fitting 5a is only cancelled when the sealing member 11 has reached the position shown in FIG. 8, it is also ensured that in an intermediate position between the nebulizing position of the sealing member 11 according to FIG. 9 and the sealing position of the sealing member 11 according to FIG. 8, the delivery fitting 5a of the nebulizer cannot be pulled out of the sealing member opening 13.

As already indicated FIG. 9, the distance d between the sealing unit 10 and the breathing air-directing unit 1 of the nebulizer-connecting device according to the invention may be shortened by virtually any amount. If the distance d is minimized, i.e. if the sealing unit 10 is arranged directly next to the breathing air-directing unit 1, virtually no dead volume forms in closed condition and the respiration air flowing through the breathing air-directing unit 1 is not impaired. In addition, the flow path for the aerosol flowing through the delivery fitting 5a from the nebulizer into the respiration air is minimized when the distance d is shortened as much as possible.

Fourth Example of an Embodiment

FIGS. 10 to 13 show a fourth example of an embodiment of a nebulizer-connecting device according to the invention for respirators or similar.

Figure 10:
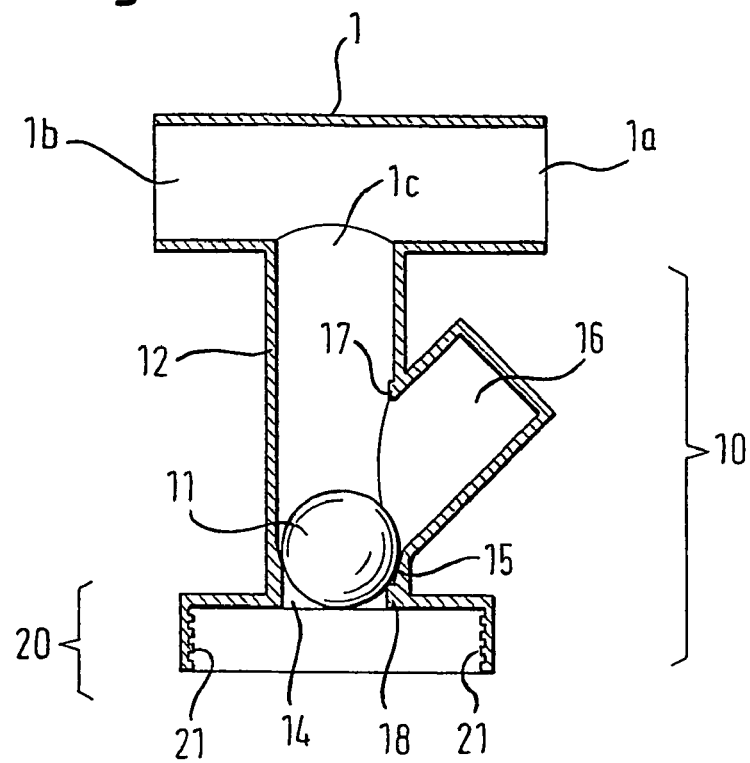
FIGS. 10 to 13 show fourth example of an embodiment of the invention.
Figure 10:
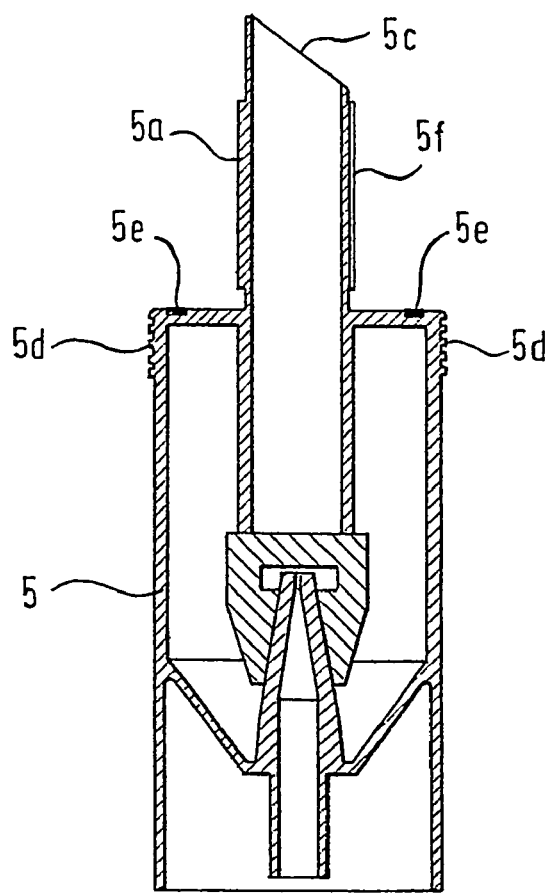

FIGS. 10 to 13 firstly show that, like the other examples of embodiments, the fourth example of an embodiment also comprises a breathing air-directing unit 1, for example the tube section 1 shown in FIG. 10, which is inserted in a duct for the respiration air supplied by a respirator and delivered to a patient. A first connecting mechanism 1a, in the simplest case one of the two tube ends, is used to connect a breathing-air duct supplying respiration air, as a rule a hose, which is connected to a respirator. A second connecting mechanism 1b is used to connect a breathing-air duct evacuating respiration air, as a rule a hose, which delivers the respiration air to the patient.

As shown in FIGS. 10 to 13, according to the invention, a sealing unit 10 is arranged on a third connecting mechanism 1c, for example the tube section 1 shown in FIGS. 10 to 13, which discharges into the breathing air-directing unit 1. The sealing unit 10 in the fourth example of an embodiment according to the invention comprises a sealing member 11, which is arranged in a sealing member housing 12. FIG. 10 shows the sealing member 11 in the position which seals the flow path of the third connecting mechanism. As shown in FIG. 10, the sealing member 11 is hereby in a position which seals the sealing member housing opening 14 of the sealing member housing 12 so that it is impossible for respiration air to enter the surroundings or surrounding air to enter the respiration air through the connector 1c. For this, the sealing area 15 of the sealing member housing 12, in which the sealing member 11 is in the sealing position, is designed as a kind of valve seat 15 resulting in a tight seal of the sealing member housing opening 14. In the fourth example of an embodiment of the invention shown here, the sealing member 11 is embodied as a ball, which, with a cylindrical sealing member housing 12, for example, is supported on an annular sealing area 15. Both the gravitation and the overpressure in the interior of the sealing member housing 12 caused by the respiration air result in a reliable seating of the ball 11 on the annular area 15 and hence in a reliable seal.

Figure 11:
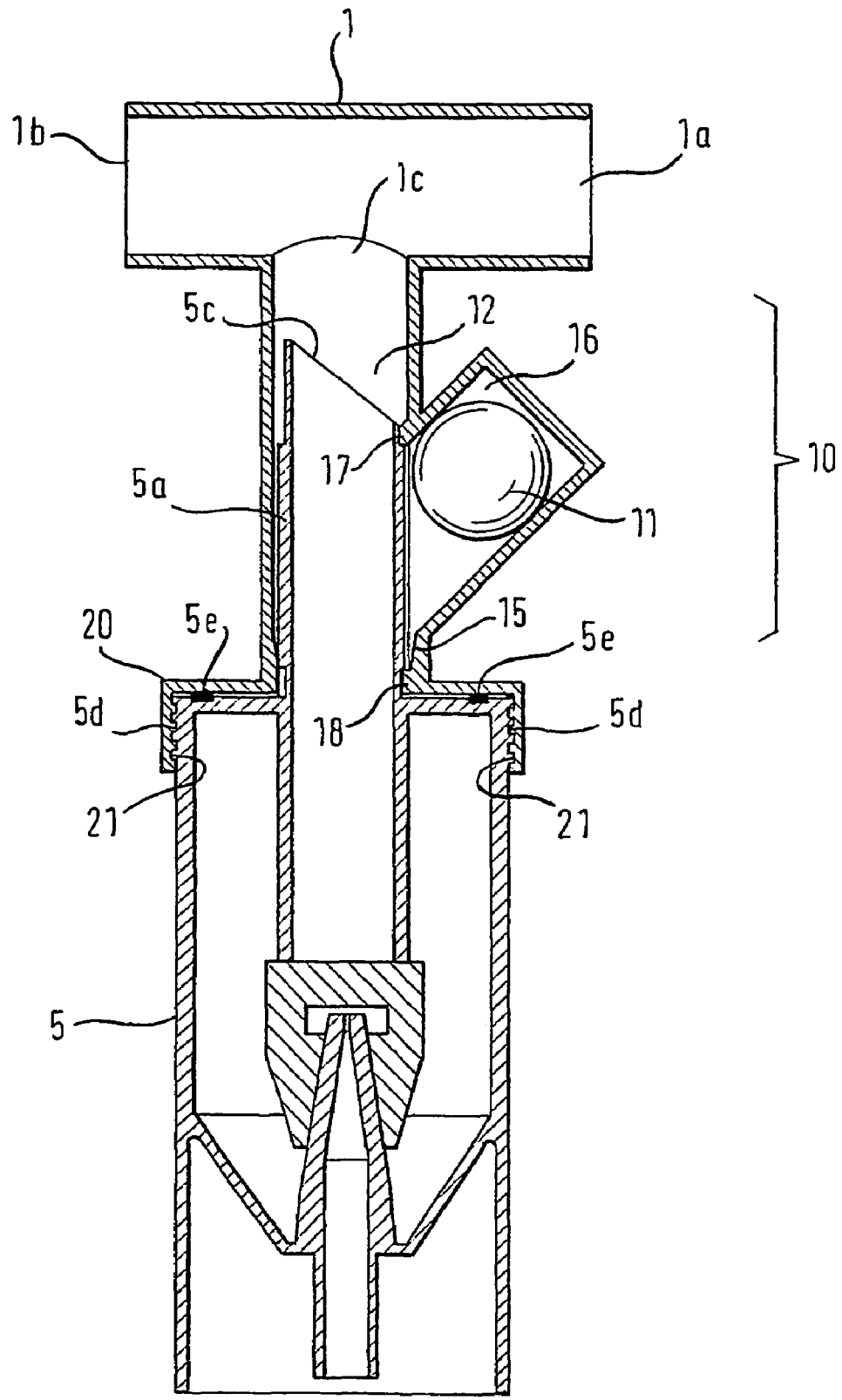

As already indicated in FIG. 10, the delivery fitting 5a of a nebulizer 5 is inserted in the sealing member housing opening 14 in order to connect the nebulizer. The delivery fitting 5a has an impact area 5c, for example in the form of a chamfered or rounded face area, which acts on the sealing member 11 when the delivery fitting 5a is inserted in the sealing member housing opening 14 and moves the sealing member 11 out of the sealing position so that the sealing member 11 is moved into a displacement area 16 provided in the sealing member housing 12 to accommodate the sealing member 11. There, the sealing member 11 is displaced by the delivery fitting 5a of the nebulizer 5 on insertion. The shape of the impact area 5c of the delivery fitting 5a ensures that the sealing member 11 reaches the displacement area 16. In addition, a deflecting projection 17 may be provided in the sealing member housing 12 to prevent the sealing member 11 entering the connector 1c. FIG. 11 shows the position of the delivery fitting 5a after insertion in the sealing member housing 12 and of the sealing member 11 in the displacement area 16.

In addition, FIGS. 10 and 11 show a nebulizer holding device 20, comprising first latching elements 21, which interact with second latching elements 5d provided on the nebulizer 5. If the nebulizer 5 is attached to the connecting device according to the fourth example of an embodiment, the latching elements 5d and 21 engage and produce a holder for the nebulizer. The action of the latching elements is such that the nebulizer can be released again from the connecting device by the action of a force that can be applied non-destructively by a person. Otherwise, the latching action is sufficient to fix the nebulizer securely.

In addition FIGS. 10 and 11 show that one or more sealing elements 5e, for example a sealing ring, can be provided on the nebulizer 5 to interact with the holding device 20 in order, in secured condition, to seal the sealing member housing 12 against the surroundings in the area of the nebulizer 5.

Figure 12:
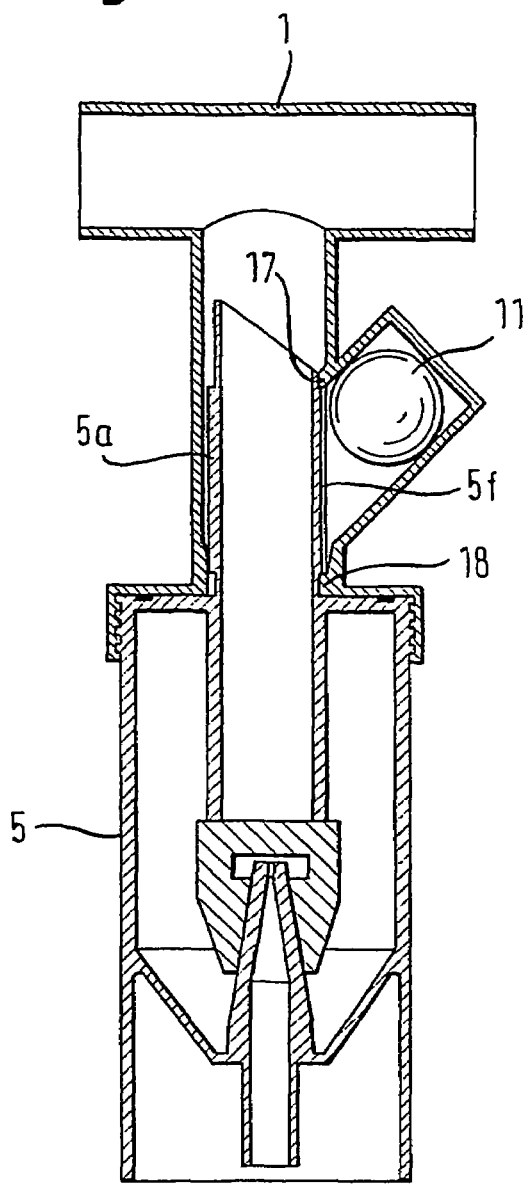
Figure 13:
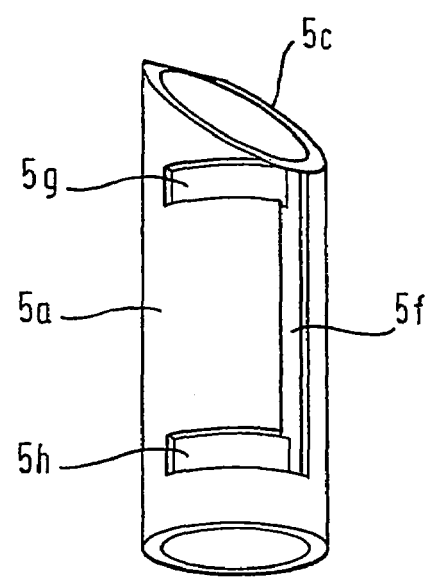
Figure 14:
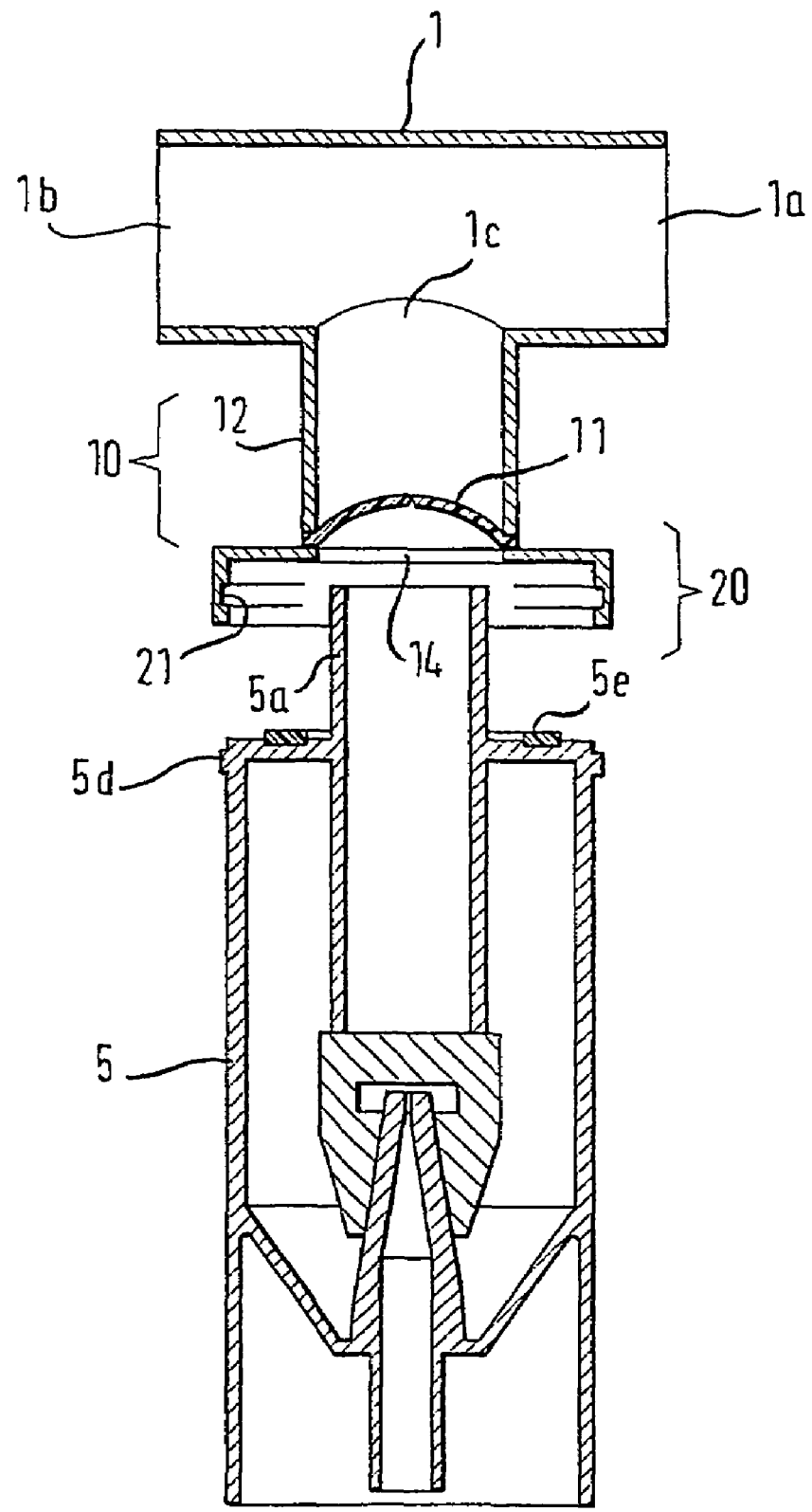
FIGS. 14 to 17 show a fifth example of an embodiment of the invention.
Figure 15:
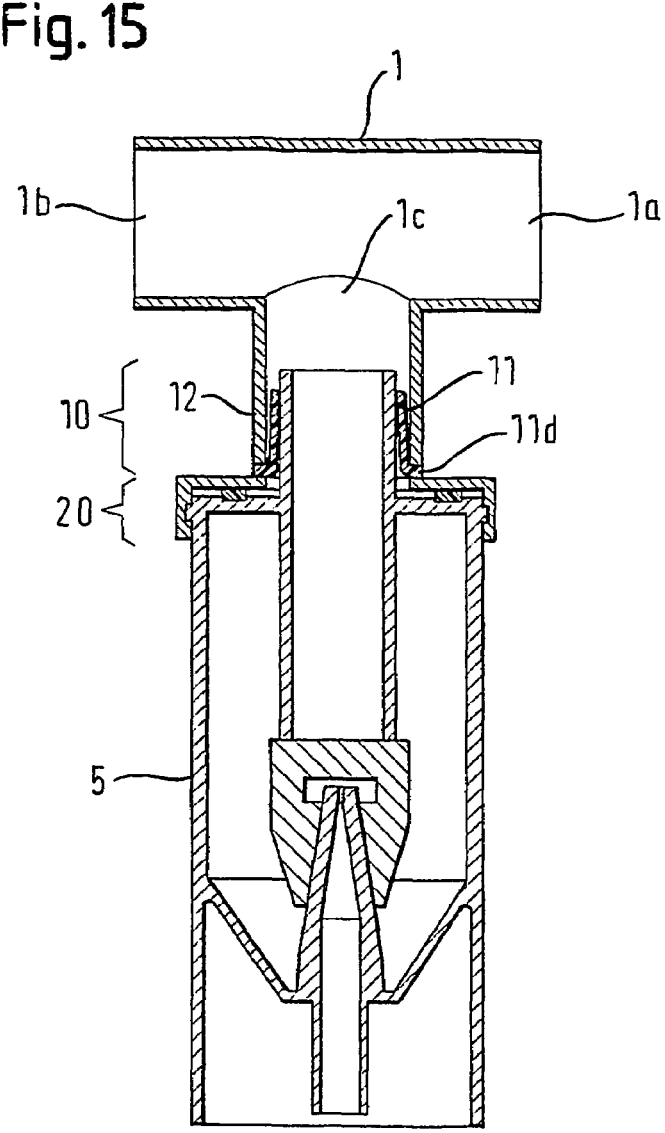
Figure 16:
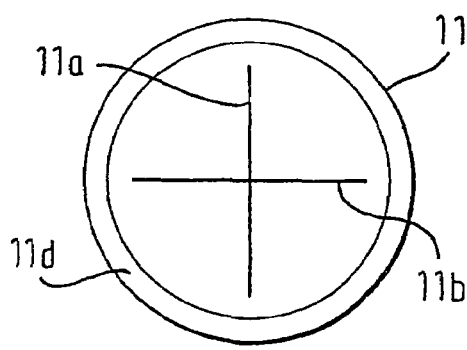
Figure 17:
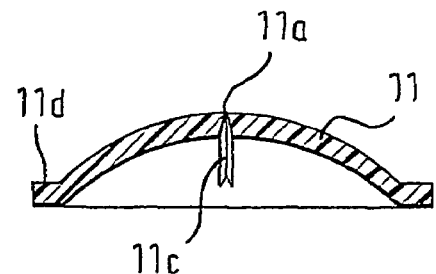

To ensure that the delivery fitting 5a can only be inserted in such a way that the impact area 5c moves the sealing member 11 into the displacement area 16, preferably an alignment groove 5f is provided on the delivery fitting 5a as shown in FIGS. 12 and 13 to interact with an alignment projection 18 in such a way that the delivery fitting 5*a* can only be inserted in the sealing member housing opening 14 when the alignment projection 18 is positioned in the alignment groove 5*f*. The alignment groove 5*f* can in addition accommodate the deflecting projection 17 if the delivery fitting 5*a* extends in inserted condition as far as shown in FIG. 12. The alignment groove 5*f* is also shown in FIG. 13 which is a picture of the aerosol delivery fitting 5*a* on its own.

FIG. 13 also shows that in the delivery fitting 5*a* first and second holding grooves 5*g* and 5*h* can be provided by means of which the nebulizer 5, alternatively or supplementarily to the latching elements shown in FIGS. 10, 11 and 12 and described above, may be held in inserted condition. This is because the holding grooves 5*g* and 5*h* interact with the deflecting projection 17 or the alignment projection 18 in the sealing member housing 12 if, after the insertion of the delivery fitting 5*a*, which by means of the alignment groove 5*d* and the two projections 17 and 18 takes place in an aligned way, the nebulizer 5 and hence the delivery fitting 5*a* are turned so that the two projections 17 and 18 enter one of the two holding grooves 5*g* and 5*h*.

Fifth Example of an Embodiment

FIGS. 14 to 17 show a fifth example of an embodiment of a nebulizer-connecting device according to the invention for respirators or similar.

FIGS. 14 to 17 firstly show that, like the other examples of embodiments, the fifth example of an embodiment comprises a breathing air-directing unit 1, for example the tube section 1 shown in FIG. 14, which is inserted in a duct for respiration air supplied by a respirator and delivered to a patient. A first connecting mechanism 1*a*, in the simplest case one of the two tube ends, is used to connect a breathing-air duct supplying respiration air, as a rule a hose, which is connected to a respirator. A second connecting mechanism 1*b* is used to connect a breathing-air duct evacuating respiration air, as a rule a hose, which delivers the respiration air to the patient.

As shown in FIGS. 14 to 17, according to the invention, a sealing unit 10 is arranged on a third connecting mechanism 1*c*, for example the tube section shown in FIGS. 14 and 15, which discharges into the breathing air-directing unit 1. The sealing device 10 in the fifth example of an embodiment according to the invention comprises a sealing member 11, which is arranged in a sealing member housing 12. FIG. 14 shows the sealing member 11 in the position which seals the flow path of the third connecting mechanism 1*c*. The sealing member of the fifth example of an embodiment is a cap-shaped valve element 11, which has two central slots 11*a* and 11*b* extending in a cross shape as shown in FIG. 16. The enlarged representation in FIG. 17 shows that on the concave side of the valve cap there is a V-shaped notch 11*c* which guarantees-optimum sealing by the valve element 11 when an overpressure is applied to the convex side of the valve cap 11. This ensures that the cap-shaped valve element 11 seals a sealing member housing opening 14 of the sealing member housing 12 so that it is impossible for respiration air to enter the surroundings or surrounding air to enter the respiration air through the connector 1*c*. The valve element 11 is suitably fixed to the sealing unit 10 at the edge 11*d*.

As already indicated in FIG. 14, the delivery fitting 5*a* of a nebulizer 5 is inserted in the sealing member housing opening 14 in order to connect the nebulizer. The delivery fitting 5*a* can, by means of the slots 11*a* and 11*b*, penetrate the valve element 11 which unblocks the flow path for the aerosol generated by the nebulizer. If the delivery fitting 5*a* of the nebulizer 5 is pulled out again, the valve element 11 closes due to its elasticity and seals the flow path as shown in FIG. 14.

In addition, FIGS. 14 and 15 show a nebulizer holding device 20 comprising first latching elements 21 which interact with second latching elements 5*d* provided on the nebulizer 5. If the nebulizer 5 is attached to the connecting device according to the fifth example of an embodiment, the latching elements 5*d* and 21 engage and produce a holder for the nebulizer. The action of the latching elements is such that the nebulizer can be released again from the connecting device by the action of a force that can be applied non-destructively by a person. Otherwise, the latching action is sufficient to fix the nebulizer securely. Instead of the latching elements, it is also possible to use a thread or another suitable type of fixing.

In addition, FIGS. 14 and 15 show that one or more sealing elements 5*e*, for example a sealing ring, can be provided on the nebulizer 5 to interact with the holding device 20 in order in secured condition to seal the sealing member housing against the surroundings in the area of the nebulizer 5.

Sixth Example of an Embodiment

FIGS. 18 and 19 show a sixth example of an embodiment of a nebulizer-connecting device according to the invention for respirators or similar.

FIGS. 18 and 19 firstly show that, like the other examples of embodiments, the sixth example of an embodiment comprises a breathing air-directing unit 1, for example the tube section 1 shown in FIG. 18, which is inserted in a duct for the respiration air supplied by a respirator and delivered to a patient. A first connecting mechanism 1*a*, in the simplest case one of the two tube ends, is used to connect a breathing-air duct supplying respiration air, as a rule a hose, which is connected to a respirator. A second connecting mechanism 1*b* is used to connect a breathing-air duct evacuating respiration air, as a rule a hose, which delivers the respiration air to the patient.

Figure 18:
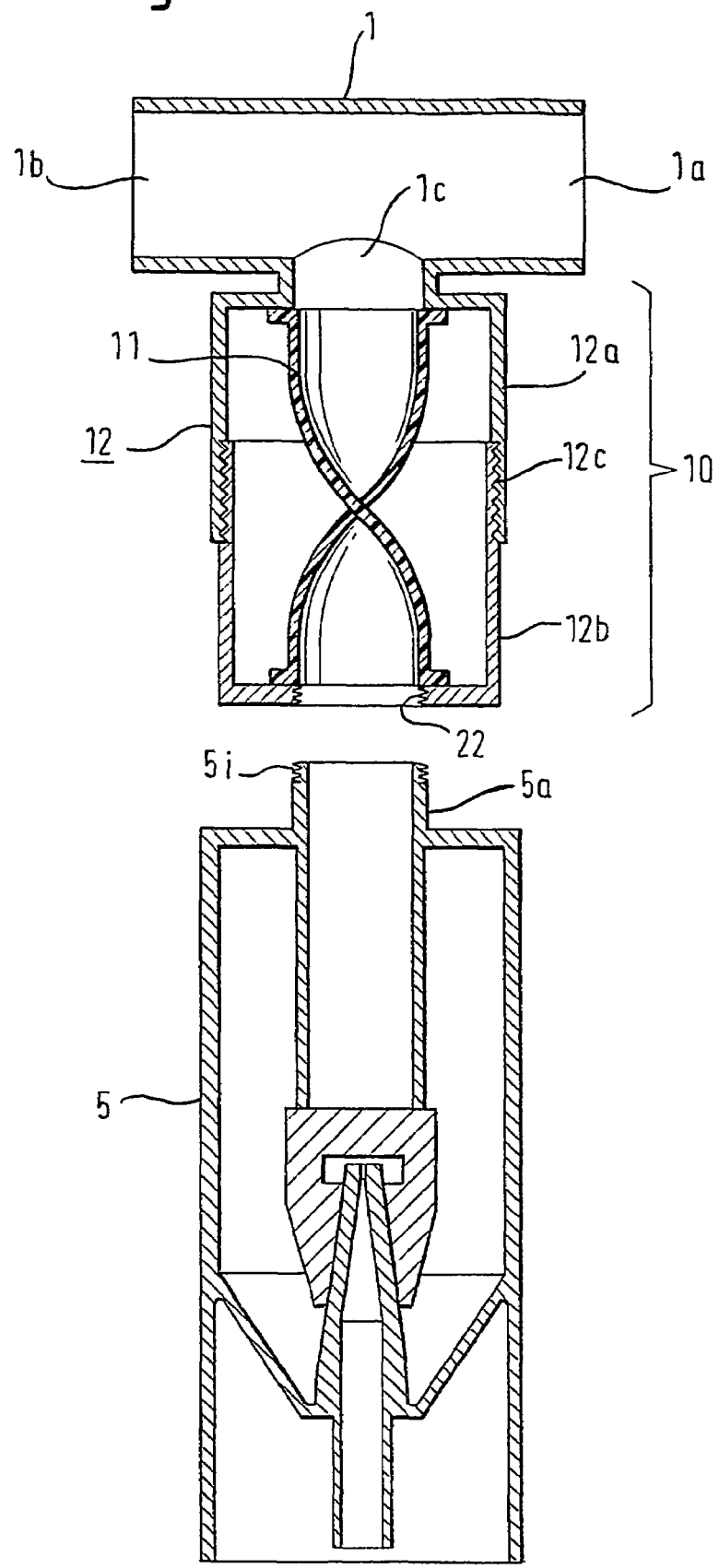
FIGS. 18 and 19 show a sixth example of an embodiment of the invention.
Figure 19:
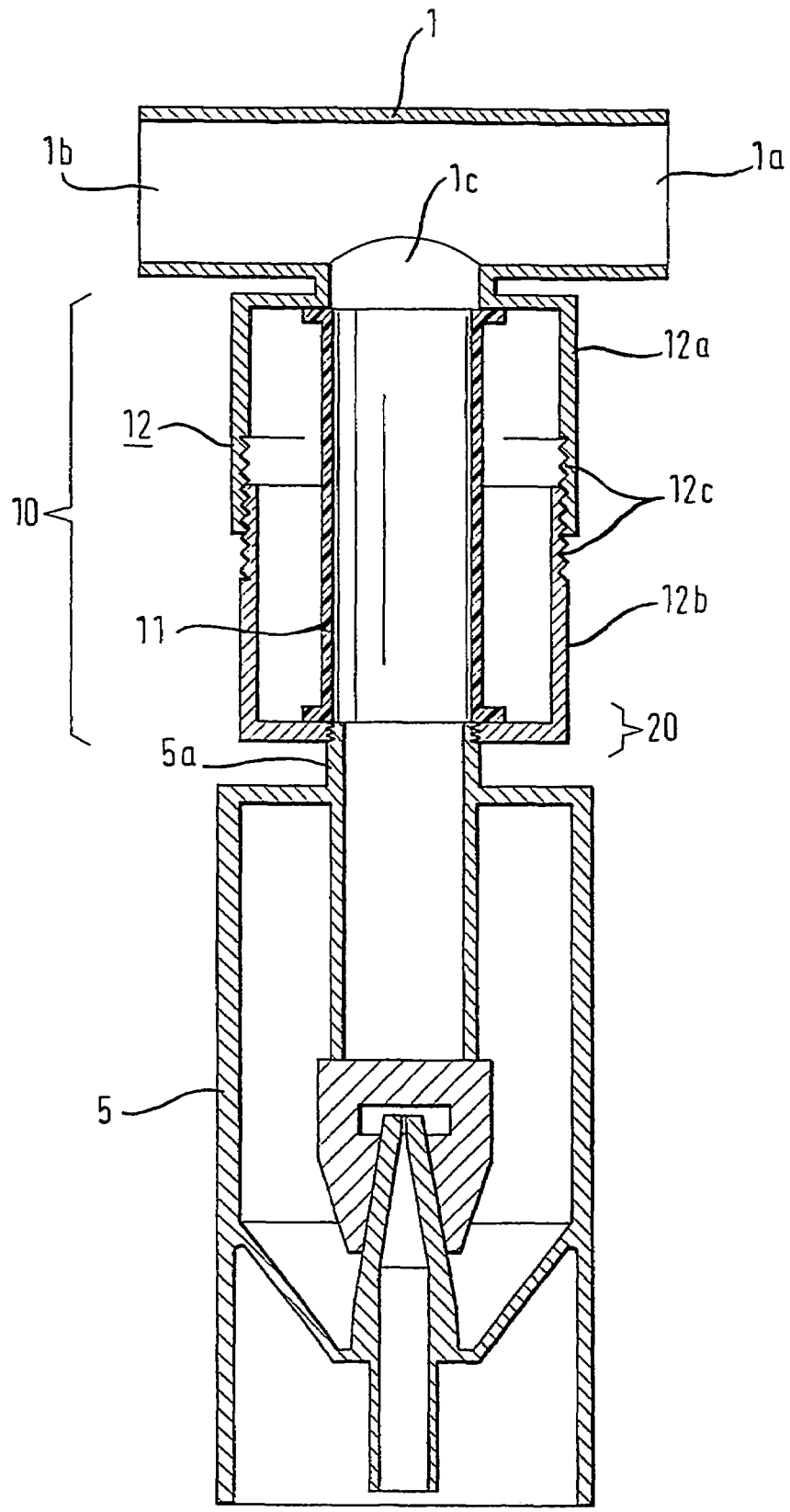

As shown in FIGS. 18 and 19, a sealing unit 10 is arranged on a third connecting mechanism 1c, for example the tube section shown in FIGS. 18 and 19, which discharges into the breathing air-directing unit 1. The sealing unit 10 in the sixth example of an embodiment according to the invention comprises a sealing member 11, which is arranged in a sealing member housing 12. FIG. 18 shows the sealing member 11 in the position which seals the flow path of the third connecting mechanism. The sealing member in the sixth example of an embodiment is a hose piece 11 which is firmly connected at one end to a first housing part 12a of the sealing member housing 12 and at the other end with a second housing part 12b of the sealing member housing 12. In the sealing position, hose part 11 is twisted far enough to ensure that the hose part 11 seals a sealing member housing opening 14 of the sealing member housing 12 so that it is impossible for respiration air to enter the surroundings or surrounding air to enter the respiration air through the connector 1c.

The two housing parts 12a and 12b of the sealing member housing 12 are connected to each other so they may be rotated in relation to each other, for example by means of two threaded areas 12c provided on areas of the two housing parts 12a and 12b facing each other. This ensures that the second housing part 12b, which is not firmly connected to the connector 1c may be rotated in relation to the first housing part 12a, which is firmly connected to the connector 1c, so that hose part 11 can be twisted out of its twisted, and hence flow-path sealing, position into a position which unblocks the flow path.

For this and to secure a nebulizer 5, an internal thread 22 is provided on the sealing member housing opening 14 into which an external thread 5i arranged on a delivery fitting 5a of the nebulizer 5 may be screwed. If the delivery fitting 5a is firmly screwed to the sealing member housing opening 14, the nebulizer 5 is firstly securely connected to the nebulizer-connecting device according to the invention. The internal thread 22 and the external thread 5i together form a nebulizer holding device 20. If the turning movement required for holding is continued, the second housing part 12b is rotated against the first housing part 12a so that the hose part is transferred from the twisted position shown in FIG. 18 into the open position shown in FIG. 19. If the nebulizer 5 is separated again from the nebulizer-connecting device, firstly a rotational movement is executed which twists the hose part 11, as shown in FIG. 18. Only then is the nebulizer 5 released in that the delivery fitting 5a is unscrewed from the sealing member housing opening 14.

Seventh Example of an Embodiment

Figure 20:
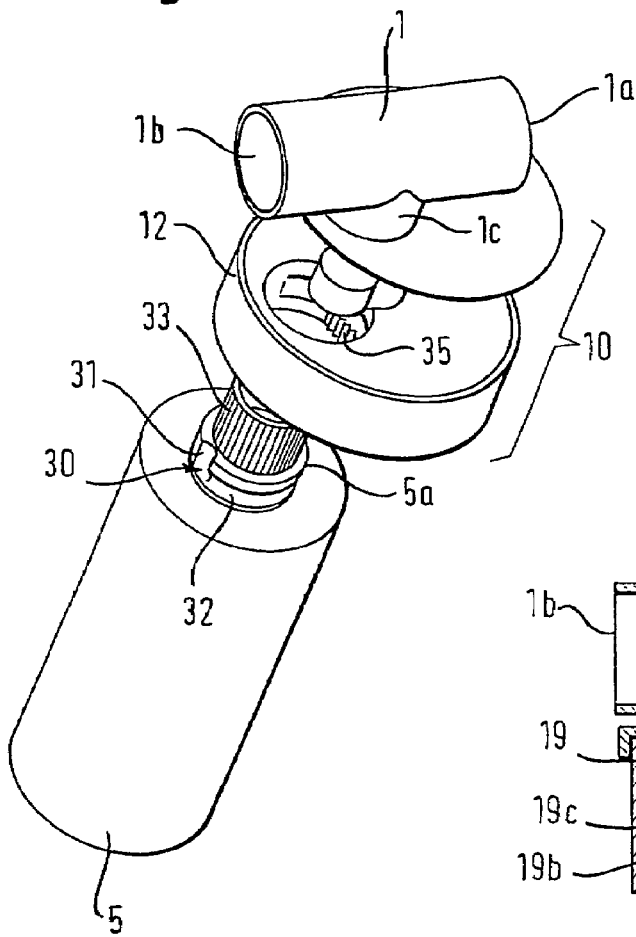
FIGS. 20 to 22 show a seventh example of an embodiment of the invention.
Figure 21:
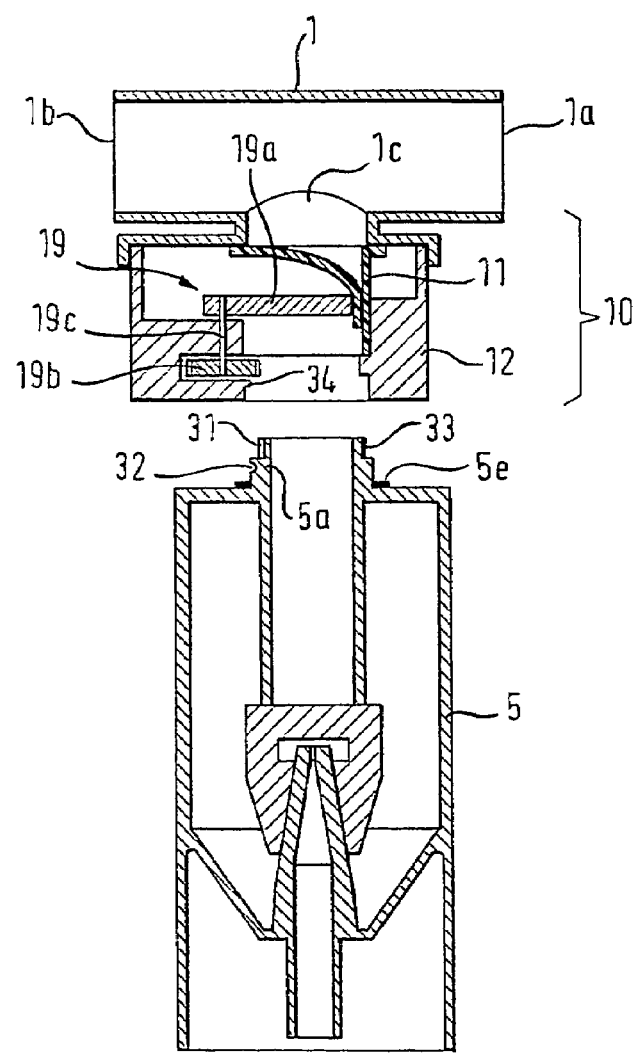
Figure 22:
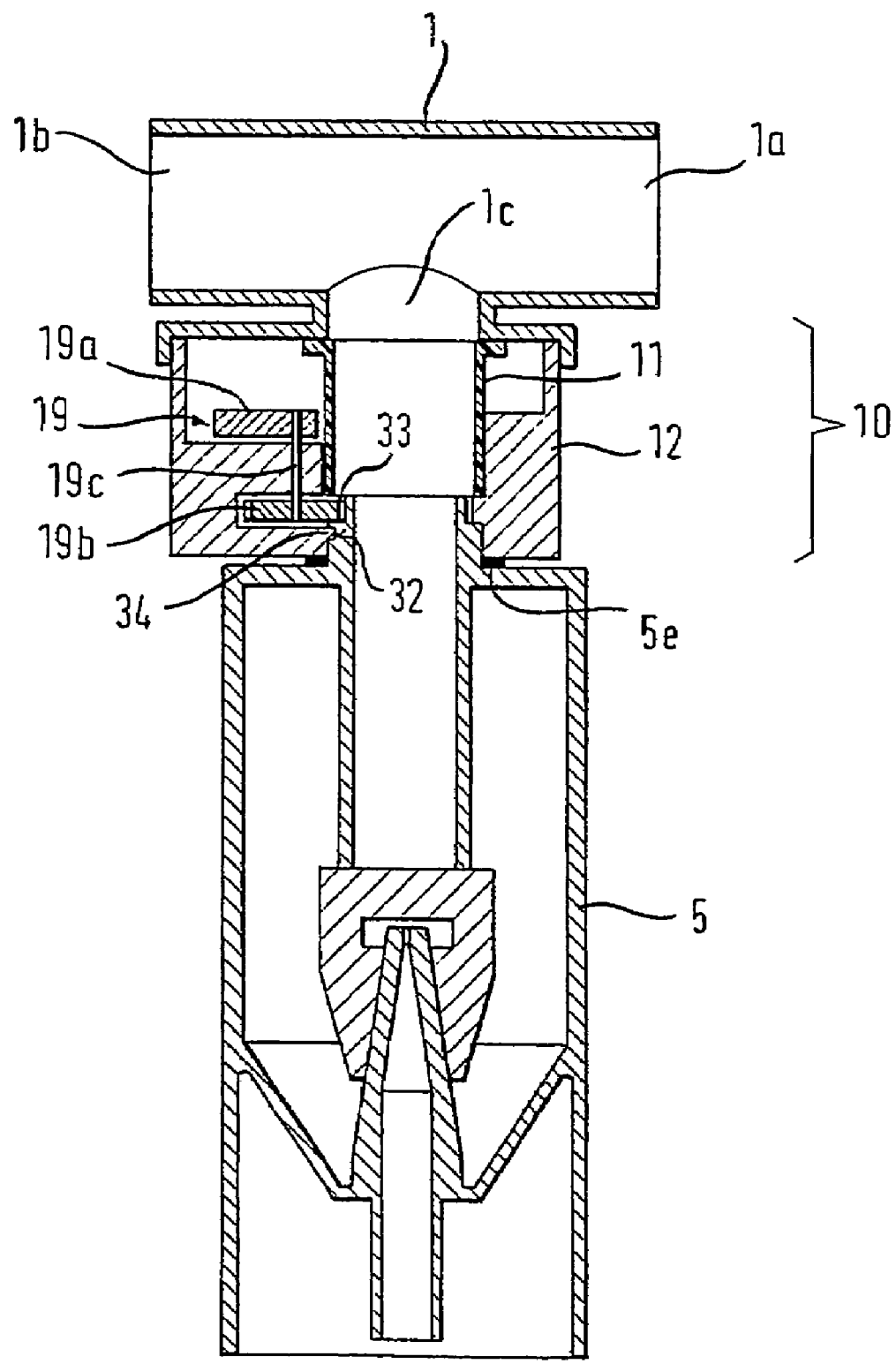

FIGS. 20 to 22 show a seventh example of an embodiment of a nebulizer-connecting device according to the invention for respirators or similar.

FIGS. 21 to 23 firstly show that, like the other examples of embodiments, the seventh example of an embodiment comprises a breathing air-directing unit 1, for example the tube section 1 shown in FIG. 20, which is inserted in a duct for respiration air supplied by a respirator and delivered to a patient. A first connecting mechanism 1a, in the simplest case one of the two tube ends, is used to connect a breathing-air duct supplying respiration air, as a rule a hose, which is connected to a respirator. A second connecting mechanism 1b is used to connect a breathing-air duct evacuating respiration air, as a rule a hose, which delivers the respiration air to the patient.

As shown in FIGS. 20 to 22, according to the invention, a sealing unit 10 is arranged on a third connecting mechanism 1c, for example the short tube section shown in FIGS. 20 to 22, which discharges into the breathing air-directing unit 1. The sealing unit 10 in the seventh example of an embodiment according to the invention comprises a sealing member 11, which is arranged in a sealing member housing 12. FIG. 21 shows the sealing member 11 in the position which seals the flow path of the third connecting mechanism. The sealing member in the seventh example of an embodiment is a short hose part 11 which is connected at one end to the sealing member housing 12. In the sealing position shown in FIG. 21, a clamping mechanism 19 clamps the hose part 11 so far together through the connector 1c that it is impossible for respiration air to enter the surroundings and surrounding air to enter the respiration air.

In the seventh example of an embodiment shown in FIGS. 21 and 22, the clamping mechanism 19 comprises a clamping element 19a, that acts directly on the hose 11 and clamps it in the sealing position, an actuating element 19b, by means of which the clamping element 19a is actuated and a connecting element 19c that establishes a connection between the clamping element 19a and the actuating element 19b. If a force acts on the actuating element 19b that turns the actuating element, the force, and hence the rotational movement, is transferred to the clamping device 19a due to the action of the connecting element 19c. In this way, the clamping element 19a is transferred from the sealing position, shown in FIG. 21 into the open position shown in FIG. 22. As shown in FIG. 22, the flow path through the connector 1c is then free to deliver an aerosol in the breathing-air flow.

To fix a nebulizer 5, a bayonet connector 30 is provided on the delivery fitting 5a of the nebulizer 5 with an insertion groove 31 extending in the longitudinal direction of the delivery fitting 5a and a locking groove 32 extending on the circumference. Provided on the sealing member housing opening 14 is a corresponding locking pin 34, which is inserted in the insertion groove 31 and moved by rotating the nebulizer 5 in the locking groove 32 in order to hold the nebulizer 5 securely on the sealing member housing opening 14. On the rotary motion of the nebulizer 5, the rotary motion is transmitted via a toothed surface 33 on the delivery fitting 5a to the actuating element 19b, which comprises corresponding teeth 35. The connecting element 19c transmits the rotary motion onto the actuating element 19a, which is swivelled out of the sealing position (FIG. 21) into the open position (FIG. 22). The hose part 11 opens as a result of the now absent clamping effect of the clamping elements 19a due to its intrinsic elasticity and unblocks the flow path for the aerosol.

If the nebulizer 5 is separated from the nebulizer-connecting device again, firstly a turning motion is executed which turns back the actuating element 19b causing the actuating element 19a via the connecting element 19c to be moved back into the clamping position and to clamp the hose 11 in a sealing way. Only then, will the nebulizer 5 be released from the nebulizer-connecting device according to the invention by separating the delivery fitting 5a from the bayonet connector 30 of the sealing member housing opening 14.

In principle, the nebulizer-connecting device according to the invention is suitable for every type of nebulizer, i.e. not only for the jet nebulizer shown in the diagrams in which an aerosol is generated by means of a compressed air nozzle, which nebulizes a liquid from a liquid reservoir. It is also possible to use ultrasonic nebulizers, but in particular membrane nebulizers in which a liquid is nebulized through a porous membrane if the membrane is caused to vibrate by a piezoelement. With the last mentioned membrane nebulizers, it may be provided that the third connecting mechanism in the breathing air-directing unit is oriented upward in use and correspondingly the sealing member housing and all other components are located above the breathing air-directing unit. An arrangement above the breathing air-directing unit and hence above the breathing-air duct may also be advantageous with other types of nebulizer. In all the cases described here, in addition, it is expedient to have a design in which the third connecting mechanism discharges not vertically but obliquely into the breathing air-directing unit in order to reduce deposition still further. This is because an oblique design of the third connecting mechanism causes the aerosol to be introduced into the breathing air-directing unit in the direction of the breathing-air flow.

The invention claimed is:

1. Nebulizer-connecting device for respirators with a breathing air-directing unit comprising:
    a first connecting mechanism for connecting a duct supplying breathing air,
    a second connecting mechanism for connecting a duct evacuating breathing air, and
    a third connecting mechanism for connecting a nebulizer,
    wherein a sealing unit is arranged on the third connecting mechanism and comprises a sealing member housing, with a sealing member arranged therein, wherein the sealing member is configured so that in a first position, the sealing member seals a flow path for an aerosol generated by a connected nebulizer and in a second position, the sealing member unblocks the flow path from an aerosol generated by a connected nebulizer, wherein the sealing member is also configured so that in the second position, the flow path is free of the sealing member such that the sealing member completely unblocks the flow path, and wherein the unblocking or sealing of the flow path for the aerosol is performed by the action of the nebulizer, or a part thereof, on the sealing unit.

2. Nebulizer-connecting device according to claim 1, wherein the sealing unit comprises a sealing member in a sealing member housing in which the sealing member is moveable by the nebulizer, or a part thereof, out of a position in which the sealing member seals the flow path of an aerosol generated by the nebulizer in the breathing air-directing unit into a position in which the sealing member unblocks the flow path of an aerosol generated by the nebulizer in the breathing air-directing unit and back.

3. Nebulizer-connecting device according to claim 2, wherein the sealing member is a cap-shaped valve element, which has at least two intersecting slots and its concave surface faces the sealing member housing opening.

4. Nebulizer-connecting device according to claim 3, wherein on the concave side of the valve element, there is a V-shaped notch on the slots.

5. Nebulizer-connecting device according to claim 3, wherein the valve element has an edge for fixing in/on the sealing member housing.

6. A nebulizer-connecting device for respirators with a breathing air-directing unit comprising:
    a first connecting mechanism for connecting a duct supplying breathing air,
    a second connecting mechanism for connecting a duct evacuating breathing air, and
    a third connecting mechanism for connecting a nebulizer, the third connecting mechanism defining an aerosol flow path and including a sealing member housing and a sealing member; and
    a nebulizer delivery fitting having an exterior surface, the fitting being inserted into the sealing member housing of the third connecting mechanism at one end and being connected to a nebulizer at a second end;
    wherein the nebulizer delivery fitting is movable from a first position to a second position, wherein:
        in the first position, the nebulizer delivery fitting exterior surface is recessed away from the sealing member such that the sealing member seals the third connecting mechanism to prevent an aerosol from the nebulizer delivery fitting from entering the aerosol flow path of the third connecting mechanism;
        in the second position, the nebulizer delivery fitting penetrates the sealing member such that the sealing member is adjacent to the exterior surface of the nebulizer delivery fitting, wherein the aerosol flow path of the third connecting mechanism is free from obstruction by the sealing member.

* * * * *